United States Patent
Doi et al.

(10) Patent No.: US 8,634,133 B2
(45) Date of Patent: Jan. 21, 2014

(54) SURGICAL MICROSCOPE WITH A MOVABLE ILLUMINATION PART

(75) Inventors: Masao Doi, Fuchu (JP); Toshio Yamazaki, Mitaka (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 424 days.

(21) Appl. No.: 12/946,148

(22) Filed: Nov. 15, 2010

(65) Prior Publication Data

US 2011/0122490 A1 May 26, 2011

(30) Foreign Application Priority Data

Nov. 20, 2009 (JP) ................................ P2009-264739

(51) Int. Cl.
*G02B 21/06* (2006.01)

(52) U.S. Cl.
USPC ............................ 359/385; 359/388; 359/372

(58) Field of Classification Search
None
See application file for complete search history.

(56) References Cited

U.S. PATENT DOCUMENTS

| | | | |
|---|---|---|---|
| 5,099,354 A * | 3/1992 | Lichtman et al. | 359/389 |
| 5,116,116 A * | 5/1992 | Aizu et al. | 351/221 |
| 8,054,543 B2 | 11/2011 | Strahle et al. | |
| 2003/0201378 A1 * | 10/2003 | Ishikawa et al. | 250/201.3 |
| 2004/0080816 A1 * | 4/2004 | Koetke | 359/368 |
| 2006/0072192 A1 * | 4/2006 | Namii | 359/389 |
| 2008/0212171 A1 | 9/2008 | Strahle et al. | |
| 2010/0142040 A1 * | 6/2010 | Hirafuji et al. | 359/385 |
| 2012/0120486 A1 | 5/2012 | Strahle et al. | |

FOREIGN PATENT DOCUMENTS

| | | |
|---|---|---|
| JP | 3-185414 | 8/1991 |
| JP | 2009-512887 | 3/2009 |

* cited by examiner

*Primary Examiner* — Arnel C Lavarias
(74) *Attorney, Agent, or Firm* — Greenblum & Bernstein P.L.C.

(57) ABSTRACT

A slit 9 having a predetermined length is formed in a mirror 8 and an illumination light L of illumination part 10 irradiates an observation area E in a manner of zero-angle illumination to an optical axis K. The illumination part is movable to form an oblique path of the illumination light L which passes through the slit 9. A shadow appears due to the oblique path of the illumination light L and it facilitates a stereoscopic observation.

3 Claims, 6 Drawing Sheets

SURGICAL MICROSCOPE WITH A MOVABLE ILLUMINATION PART

BACKGROUND OF THE INVENTION

The present invention relates to a surgical microscope. The surgical microscope is used to view an objective such as a surgical observation area by an enlarged image thereof during an operation. An illumination part is arranged in a microscope body and irradiates the objective with light beam. A reflected light beam radiated by the illumination part is introduced into the microscope to create a magnified image for viewing.

In a case where the objective is a dimpled or hollow portion having a narrow opening with respect to its depth, the illumination light should approach a target that is a bottom portion substantially along a viewing axis defined by an objective lens in order to reach the target. This fashion of illumination is called as a zero-angle illumination.

A related system of the zero-angle illumination is disclosed in US2008212171A1. The illumination system of the related art employs a mirror arranged in an inlet for introducing a light flux of the objective and positioned on an optical axis so that the reflected light ray traveling along the optical axis is bent by a right angle. The light beam emitted from the illumination part passes through an opening formed in the mirror and approaches the target along the optical axis in a manner of the zero-angle illumination.

SUMMARY OF THE INVENTION

Due to the related art, the illumination light beam passing through the opening is able only to reach an area of the objective right on the optical axis. That is preferable to view a bottom of a narrow or deep portion. However, there is a demerit in viewing a smooth portion such as a rolling portion or a plane portion. In this case, the illumination light hits the portion substantially to the normal, that is, a shadow due to its shape is not formed, thereby, it is hard to perform a stereoscopic viewing.

In consideration of the related art, the present invention provides a surgical microscope capable of an oblique illumination as well as the zero-angle illumination.

According to a first aspect of the present invention, a surgical microscope comprising a mirror configured to introduce a reflected light of an objective traveling along a primary axis of an inlet portion being disposed under the mirror and reflect it substantially at a right angle, a slit forted in the mirror wherein the primary axis of the inlet portion crosses therethrough, and an illumination portion configured to irradiate the objective through the slit and the inlet portion wherein the illumination portion is movable so that an illumination light being in a virtual plane defined by the primary axis of the inlet portion and a primary axis of the slit.

According to a second aspect of the present invention, a surgical microscope comprising a mirror reflecting light rays reflected at an objective and passed through an inlet portion being disposed under the mirror wherein a reflected light ray of the objective approaches along a principal axis of the inlet portion, strikes the mirror, and is bent substantially at a right angle, an aperture formed in the mirror on the principal axis of the inlet portion, at least one supplemental aperture formed in the mirror so that the principal axis of the inlet portion, the aperture, and the supplemental aperture define a virtual plane, and an illumination portion configured to irradiate the objective through the slit and the inlet portion wherein the illumination portion is movable so that illumination light rays pass through one of the aperture and the supplemental aperture.

DESCRIPTION OF THE PREFERRED EMBODIMENT

First Embodiment

Figure 1:
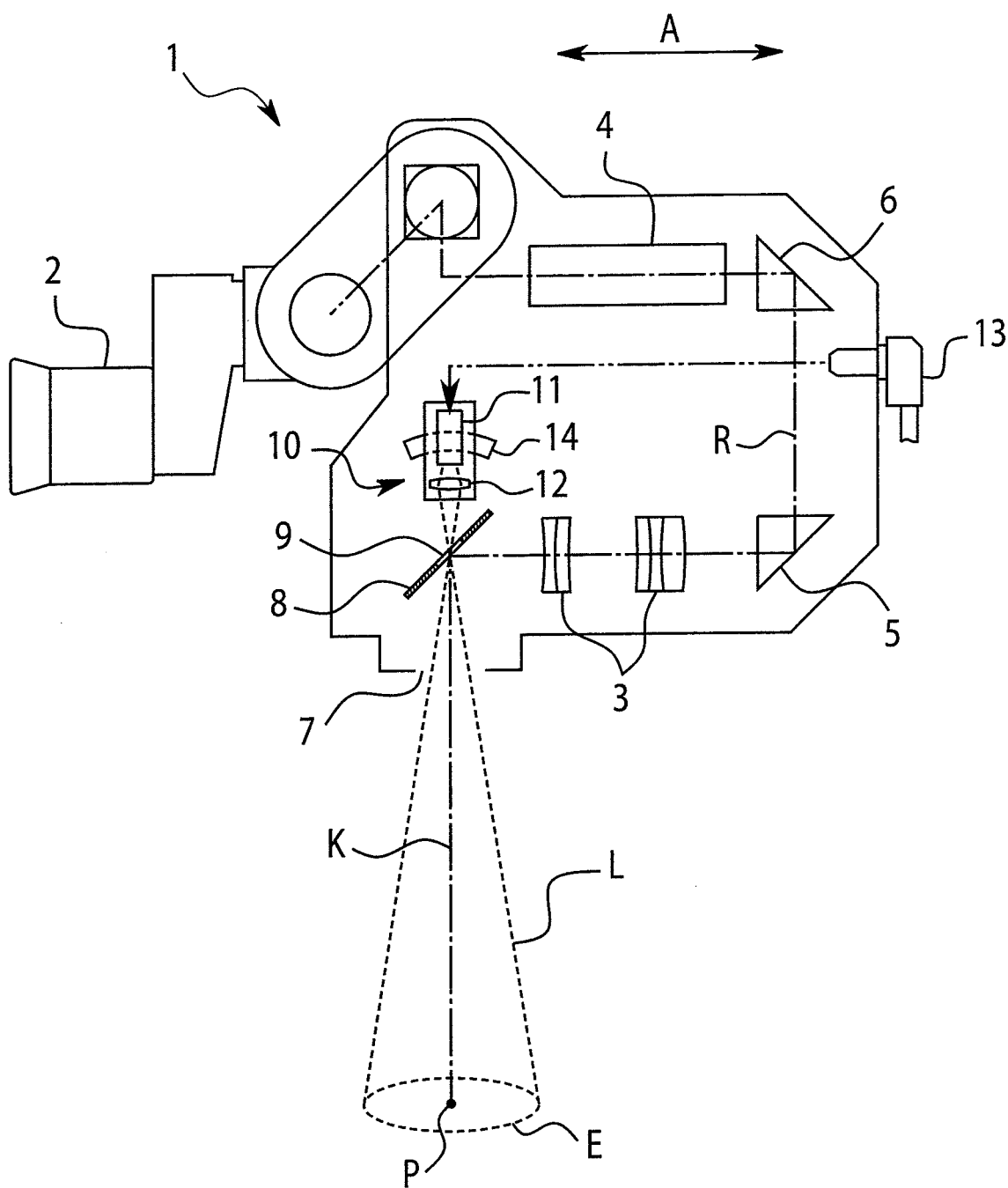
FIG. 1 is a schematic representation of a surgical microscope according to First Embodiment.
Figure 2:
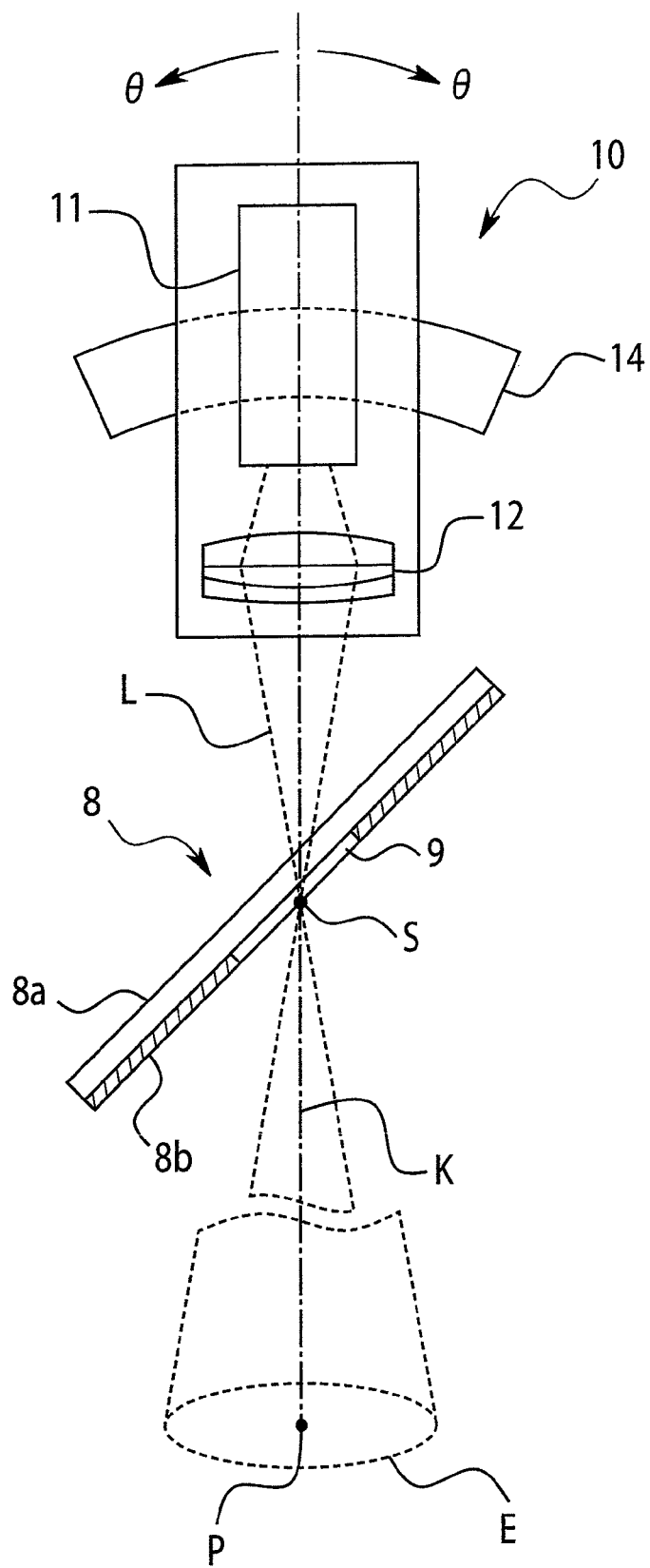
FIG. 2 illustrates a side view of a mirror and an illumination portion.

The first preferred embodiment of the present invention will be explained with reference to FIGS. 1 to 5. Hereafter, an arrow A as depicted in FIG. 1 represents a direction of forward and backward and then a direction perpendicular to the arrow A in a horizontal plane is to right and left.

A surgical microscope 1 is supported by an arm of a stand apparatus (not illustrated) which is installed in a surgery room. The surgical microscope 1 is a stereoscopic microscope having two eyepiece portions 2. Inside the body of the surgical microscope, a focal lens 3 is disposed at a lower side and a zoom lens 4 is disposed at an upper side and each arranged along the forward and backward direction on the horizontal plane. Prisms 5, 6 are arranged at an end of the focal lens 3 and an end of the zoom lens 4 respectively.

An inlet portion 7 to introduce light from an observation area E through a window is formed at a lower side under the eyepiece portion 2 of the surgical microscope 1. Reflected light from the observation area E enters the inlet portion 7 along an optical axis K defined by the inlet portion 7 and the observation area E is viewed by the surgical microscope 1.

A plane mirror 8 being circular in diameter is disposed above the inlet portion 7 and the normal is positioned at an angle of 45 degrees with respect to the optical axis K. The plane mirror 8 is formed by an argent mirror layer 8b evaporated on a glass 8a except for a slit portion 9. The slit portion 9 is optically transparent and is an elongate opening formed in the mirror 8 where the argent mirror layer is absent. The slit portion 9 is arranged in the forward and backward direction A and has an elongate shape with a predetermined length along its principal axis. The slit portion 9 is a part of the glass plate 8a without the mirror layer and is optically transparent. In other words, the principal axis of the slit portion 9 is defined in a predetermined virtual plane including the optical axis K.

An illumination part 10 is arranged above the mirror 8. The illumination part 10 includes an end portion of an optical fiber 11 and a converging lens 12. Illumination light rays L passing through an optical fiber plug 13 which is attached to the surgical microscope 1 are introduced into the end portion of the optical fiber 11 through an optical fiber (not illustrated). Thus the illumination light L is radiated downward.

The illumination part 10 is movably supported by an arc shaped rail 14, and thereby, is able to tilt and slide along the rail 14 which defines a virtual arc around a point P of an optical axis K on the observation area E. Rheterfore, the illumination part 10 is movable along a Circular are centered on the observation area E on the principle axis of the inlet portion 7. The virtual arc of the rail 14, a principal axis of the slit, and the optical axis K as well as the point P on the observation area E are included by a predetermined virtual plane. That is, the rail 14 is arranged in parallel with a primary axis of the slit portion 9, i.e. in the direction A. An optical axis of the illumination emitted by the illumination part 10 is inclinable within a predetermined angle θ with respect to the optical axis K in the direction A. The illumination part 10 can be tilted during sliding along the rail 14 by way of a tilting mechanism including a reduction gear and an actuator that is a motor (not illustrated).

The illumination light L radiated downward by the illumination part 10 is converged at a converging point S via a converging lens 12, and then spreads to irradiate the observation area E. An optical configuration is designed so that the converging point S is positioned just at the slit 9 as the illumination part 10 is at a normal position with the optical axis thereof coinciding with the optical axis K. This results in substantially free of loss in light flux at the slit portion 9.

The illumination light L passing through the slit portion 9 irradiates the observation area E in a manner of the zero-angle illumination. This enables irradiating of a deep or narrow area E.

Figure 3:
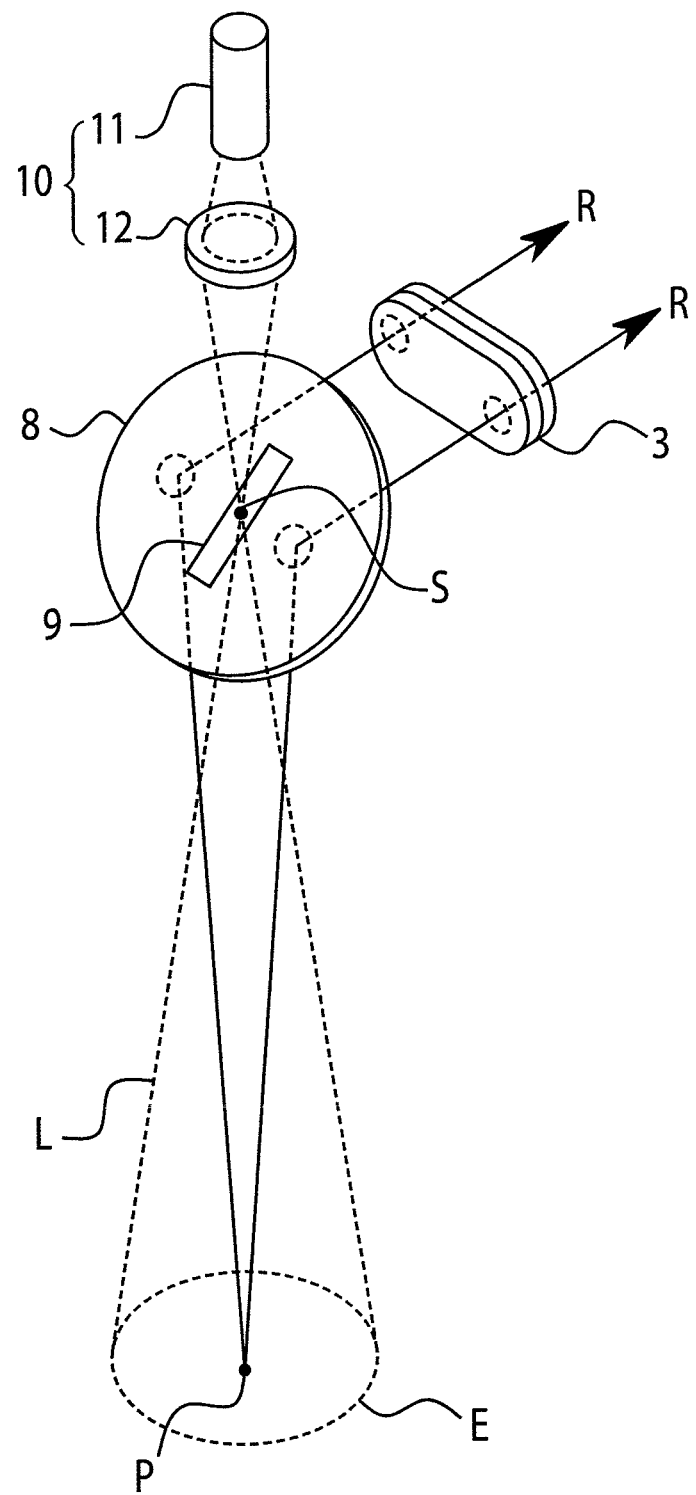
FIG. 3 illustrates a perspective view of a mirror and an illumination portion.
Figure 4:
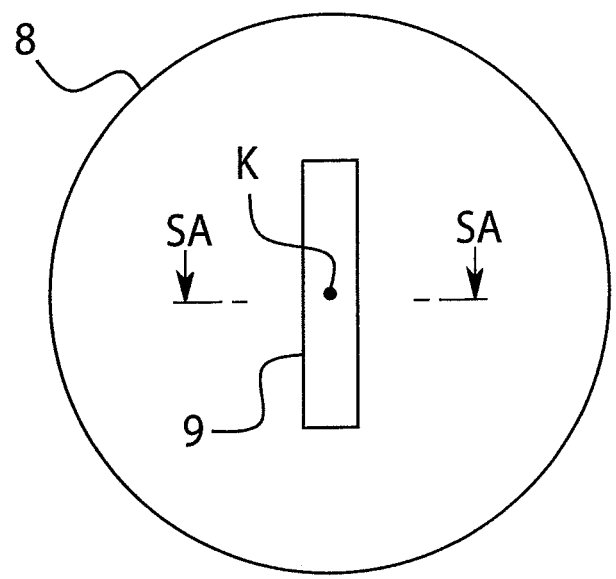
FIG. 4 illustrates a plane view of a mirror.
Figure 5:
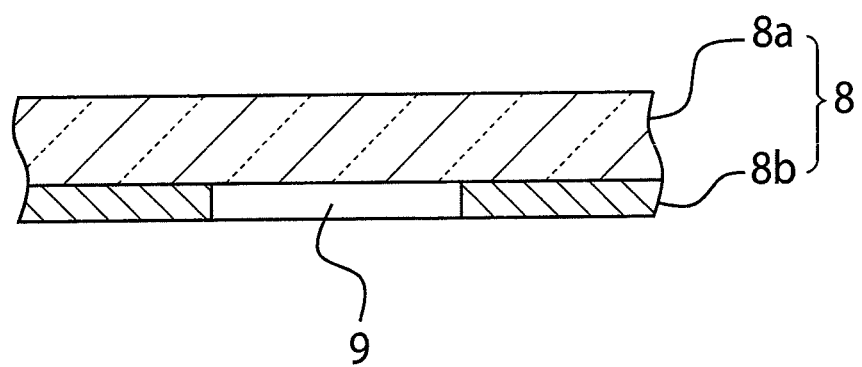
FIG. 5 illustrates a section view along SA-SA of FIG. 4.

A reflected light R from the irradiated area E is introduced in the surgical microscope 1 via the inlet portion 7. As illustrated in FIG. 3, a path of the reflected light R is bent with the right angle at the mirror 8 except for the slit portion 9. The light path R goes through a focusing optics 3, prisms 5 and 6, a zoom optics 4 to reach the eyepiece portions 2 for stereoscopic viewing of the observation area E.

In a case of a stereoscopic viewing of a smoothed surface E, the illumination part 10 is slid along the arc of the rail 14. The optical axis of the illumination light slants with respect to the optical axis K while an intersection P of the axes is substantially fixed. As a result, a shadow due to a shape of the observation area E appears thereon and this facilitates the stereoscopic viewing. Although, the optical axis of the illumination light L crosses the slit portion 9 in a slanted manner, the converging point S usually stays at a vicinity of the slit 9. This leads to free of energy loss at the slit portion 9.

According to the first embodiment, the illumination light is radiated along the optical axis K through the slit 9 to irradiate the observation area E in a manner of the zero-angle illumination. Furthermore, the illumination part is optionally tilted to facilitate the stereoscopic viewing of the observation area E. Even in this case, the optical axis of the illumination light is oriented to the point P on the observation area E at any time. That is, the illuminated area does not move from its initial position.

Second Embodiment

Figure 6:
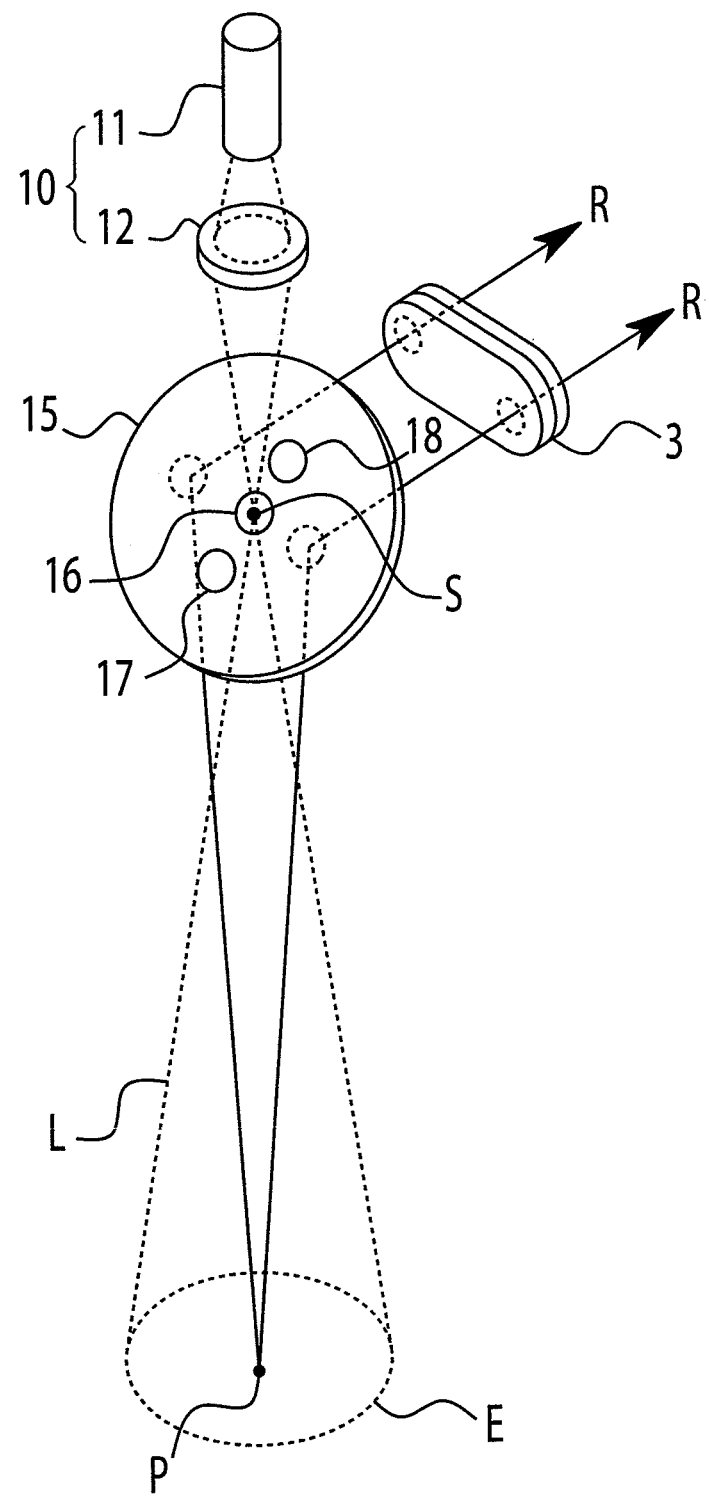
FIG. 6 illustrates a perspective view of a mirror and a illumination portion according to Second Embodiment.
Figure 7:
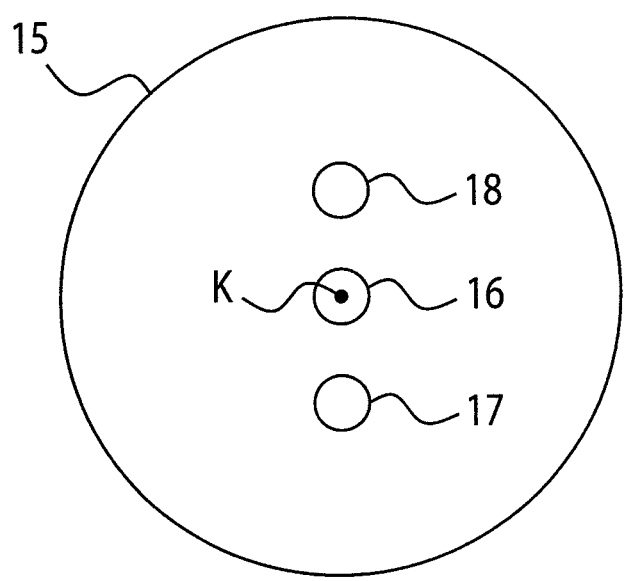
FIG. 7 illustrates a plane view of a mirror.

FIGS. 6 and 7 illustrate a surgical microscope according to a second embodiment of the present invention. The present embodiment employs structural elements that are similar to those of the first embodiment. The similar structural elements are represented with cannon reference marks to omit a repetition of explanations.

An aperture 16 as a transparent spot is formed in a mirror 15 at a position coinciding with the optical axis K. That is, the mirror layer corresponding the aperture is not formed on a glass base. Also supplemental apertures 17, 18 are formed across the aperture 16. The aperture 16 and the supplemental apertures 17, 18 arrange in a straight line and these constitute an opening part formed in an elongate area for transmitting the illumination light L. The virtual arc of the rail 14, an alignment line of the apertures 16-18, and the optical axis K as well as the point P on the observation area E are included by a predetermined virtual plane.

In a case where the observation area E is narrow or deep, the illumination light L of the illumination part 10 irradiates the observation area E through the aperture 16 wherein the optical axis K crosses it. The illumination light L passing through the aperture 16 irradiates the observation area E in a manner of the zero-angle illumination and thereby even a bottom of a hollow area E can be surely illuminated.

In a case of a stereoscopic viewing of a smoothed area, the illumination part 10 is moved so as to radiate the illumination light L through one of the supplemental apertures 17 and 18 in the slanted manner. The pass defined by the illumination light L passing through the supplemental aperture has typically a predetermined angle of 4 degree with respect to the optical axis K. As a result, a shadow of the observation area E due to the oblique angle appears thereon to facilitate the stereoscopic viewing. The illumination light L does not pass through a whole area of the opening that distributes in an elongate area, but passes only limited transmission area that is the aperture. This configuration suppresses scattering of the scattered illumination light about at the mirror 15 and thus observation through the light R is not disturbed. The slanted optical axis of the illumination light L orients the point P due to the tilting mechanism including the rail 14 at any time.

Although the slit portion 9 and the aperture 16 is formed on the mirror 15 as defined by an area without a reflection layer, a physical opening hole or cutout is also employed as the slit or the aperture.

The illumination part 10 is moved along the arc shaped rail according to the present embodiment, but can be moved along a linear rail.

The focusing optics 3 can be also arranged between the mirror 8 or 15 and the observation area E in a vertical position.

EFFECT OF THE INVENTION

As mentioned above, according to the first aspect of the present invention, a slit is formed in the mirror portion so that a hollow portion with a narrow or deep space can be easily observed in a manner of the zero-angle illumination. As the illumination part is moved off the optical axis, a smoothed portion is illuminated in the slanted manner so that a shadow appears thereon to facilitate a stereoscopic viewing. Furthermore, substantially whole illumination light passes through the slit and little loss caused at the slit.

According to the second aspect of the invention, an aperture and supplemental apertures can be employed instead of the slit, besides of the merits of the first aspect of invention, observation is not disturbed by scattering at the mirror because the scattering is suppressed due to the apertures.

This application claims benefit of priority under 35USC §119 to Japanese Patent Application No. 2009-264739, filed on Nov. 20, 2009, the entire contents of which are incorporated by reference herein. Although the invention has been described above by reference to certain embodiments of the invention, the invention is not limited to the embodiments described above. Modifications and variations of the embodiments described above will occur to those skilled in the art, in light of the teachings. The scope of the invention is defined with reference to the following claims.

What is claimed is:

1. A surgical microscope, comprising:
   a mirror configured to introduce a reflected light, from an observation area, traveling along a principal axis of an inlet portion disposed under the mirror and reflect the reflected light substantially at a right angle;
   a slit formed in the mirror, the principal axis of the inlet portion crossing therethrough; and an illumination part configured to irradiate the observation area through the slit and the inlet portion, the illumination part being movable so that an illumination light travels in a virtual plane defined by the principal axis of the inlet portion and a principal axis of the slit.

2. The surgical microscope according to claim 1, wherein the illumination part has a converging optics and a converging point thereof is defined in the slit; and the illumination light hits the converging point and travels toward the observation area.

3. The surgical microscope according to claim 2, wherein the illumination part is movable along a circular arc centered on the observation area and on the principal axis of the inlet portion.

* * * * *